US007258799B2

(12) United States Patent
Ras et al.

(10) Patent No.: US 7,258,799 B2
(45) Date of Patent: Aug. 21, 2007

(54) METHOD AND APPARATUS FOR MAGNETIC SEPARATION OF PARTICLES

(75) Inventors: Christopher A. Ras, Arlington Heights, IL (US); Gareth P. Hatch, East Dundee, IL (US)

(73) Assignee: Dexter Magnetic Techologies, Inc., Fremont, CA (US)

( * ) Notice: Subject to any disclaimer, the term of this patent is extended or adjusted under 35 U.S.C. 154(b) by 116 days.

(21) Appl. No.: 10/349,771

(22) Filed: Jan. 22, 2003

(65) Prior Publication Data

US 2003/0146166 A1 Aug. 7, 2003

Related U.S. Application Data

(60) Provisional application No. 60/350,865, filed on Jan. 22, 2002.

(51) Int. Cl.
*B01D 21/26* (2006.01)
*G01N 33/53* (2006.01)
*B03C 1/02* (2006.01)

(52) U.S. Cl. .................. 210/695; 210/222; 209/223.1; 435/288.4; 435/305.2; 422/101; 422/186.01

(58) Field of Classification Search ............... 210/222, 210/695; 209/223.1; 435/288.4, 305.2; 436/526, 809; 422/101, 186.01
See application file for complete search history.

(56) References Cited

U.S. PATENT DOCUMENTS

| 3,873,448 | A | * | 3/1975 | Isberg et al. ................ 210/222 |
| 4,110,222 | A | * | 8/1978 | Watson ....................... 210/222 |
| 4,438,068 | A | * | 3/1984 | Forrest ....................... 436/526 |
| 4,895,650 | A | * | 1/1990 | Wang .......................... 210/222 |
| 4,988,618 | A | * | 1/1991 | Li et al. ...................... 210/222 |
| 5,567,326 | A | * | 10/1996 | Ekenberg et al. ............ 210/695 |
| 5,571,481 | A | * | 11/1996 | Powell et al. ................ 210/222 |
| 5,759,407 | A | * | 6/1998 | Gurevitz ..................... 210/695 |
| 5,779,907 | A | * | 7/1998 | Yu .............................. 210/695 |
| 6,193,892 | B1 | * | 2/2001 | Krueger et al. ............. 210/695 |
| 6,514,415 | B2 | * | 2/2003 | Hatch et al. ................ 210/695 |
| 6,514,416 | B1 | * | 2/2003 | Harradine et al. .......... 210/695 |

* cited by examiner

*Primary Examiner*—David A. Reifsnyder
(74) *Attorney, Agent, or Firm*—Blakely Sokoloff Taylor & Zafman LLP

(57) ABSTRACT

A magnetic circuit is shaped to generate an essentially uniform magnetic field parallel across the length of a container, and an essentially uniform magnetic field gradient along the length of the container as well. The dot product of the magnetic field and magnetic field gradient, known as the relative force density, is substantially uniform over the entire container, thereby causing particles to uniformly separate throughout the container.

23 Claims, 6 Drawing Sheets

METHOD AND APPARATUS FOR MAGNETIC SEPARATION OF PARTICLES

This application claims the benefit of provisional application No. 60/350,865, filed Jan. 22, 2002.

FIELD OF INVENTION

The present invention generally relates to the use of magnetic fields. More specifically, the present invention relates to the magnetic separation of particles in a solution.

BACKGROUND OF THE INVENTION

The use of high gradient magnetic fields for the separation of particles is commonplace in the fields of biology, biotechnology, and other bio-medical fields. Target particles, comprising entities such as proteins and the like, may be separated from a solution by a technique known as magnetic separation.

In general, magnetic separation of specifically sought after biological entities involves coating small magnetically susceptible paramagnetic, super paramagnetic, or ferromagnetic, materials with a chemical-specific substance (e.g., a ligand that is known to chemically bond with target entities). These coated materials are referred to hereinafter as beads. The beads are introduced into a well containing a hydrous solution of the sought after, or target, entities, and unwanted biological material. Cells, proteins, nucleic acid sequences and the like are examples of target entities. The target entities chemically bond to the coating of the beads. Magnets are placed near the well to apply magnetic fields in the well and the solution. Although it is the presence of substances and other coatings that ultimately interact with the target entities, it is the characteristics of the magnetic field that is applied and physical characteristics of the beads that determine the separation time and the uniformity of the profile of the separated beads. A uniform bead separation profile is desirable, such as a profile in which the beads uniformly distribute about the base of each well to produce a "flat" profile, or in which the beads pull to the sides of the wells equally at every location.

The beads, including the target entities chemically bonded to the coating of the beads, are attracted to the magnets. The magnetic configuration corresponds well with the analytical equation which states that the resultant force on the beads (F) is proportional to the magnitude of the magnetic field (B) multiplied by its gradient ($\nabla B$).

$$F \propto B \cdot \nabla B \quad (1)$$

For the case of bead separation within a multi-well tray, the hydrous solutions in each well are physically divided. Consequently, to obtain a "uniform" distribution of beads (assuming that each well is using the same size beads, density of beads, and volume of solution) along the entire base of the tray, the above two components (B and $\nabla B$) of the force equation (1) are equal throughout the active volume of the tray, but not necessarily equal to each other. This can be accomplished by shaping a magnet to provide a uniform magnetic field and gradient parallel to the base of each well within the tray. FIG. 1 represents one such configuration.

In the case of positive separation, that is, where the sought after entities are attracted to the beads, once the beads have been collected at the desired location, the well is rinsed, removing the solution and unwanted particles. The collected beads with the target entities chemically bonded to the coating of the beads remain in the well as long as the magnetic fields are applied.

Once the well has been rinsed, a "clean" solution, without unwanted particles, is introduced into the well. A chemical is mixed with the "clean" solution to break the chemical bonds between the target entities and the coating of the beads, resulting in a well with isolated target entities. Additionally, the beads may be removed by disabling/removing the magnetic fields from the well.

In the case of negative separation, that is, where the unwanted entities are attracted to the beads and the sought after entities removed, once the beads have been collected at the desired location, the well is rinsed, removing the solution and sought after particles. The collected beads with the unwanted entities chemically bonded to the coating of the beads remain in the well as long as the magnetic fields are applied.

Molecular biological magnetic separation is well known, and until relatively recently, this process was performed using large tubes of fluids (e.g., 15–50 ml tubes) and beads. Recent molecular magnetic separation techniques typically involve the use of 96-well micro-plates, that is, a tray having 96 wells, arranged in an 8×12 matrix, with each well capable of holding 250–500 micro-liters ($\mu l$) of liquid. In another embodiment of the invention, each well may be capable of holding more than 250–500 micro-liters of liquid. A variety of placement methods for magnets to apply the desired magnetic fields may be employed on these micro-plates. One method is to place small magnets, having predetermined magnetic fields, between micro-plate receiving orifices, so that the beads collect along the walls of the wells. Another method is to place an apparatus with magnetic pins into the wells with the beads collecting on the pins. Another method is to have a base for a micro-plate with cylindrical magnets positioned for insertion from the base of the micro-plate into the spaces between the wells of the micro-plate with the beads collecting along the walls of the wells.

As molecular magnetic separation techniques advance, the number of wells increase. In high throughput applications, typically involving automated systems, 384-well to 1536-well micro-plates are utilized to increase capacity and throughput. In such systems, each 384-well micro-plate is arranged as 16×24 wells, while each 1536-well micro-plate is arranged as 32×48 wells, effectively increasing the throughput of the conventional 96-well micro-plate by 4 and 16 times respectively.

As the number of wells increase, the spaces between the individual wells in micro-plates decrease, in some cases, to the point where there is no space between the wells, making the placement of magnets between rows of wells impracticable. However, magnets are still required to separate the target particles from the solution contained in micro-plates.

BRIEF DESCRIPTION OF THE DRAWINGS

The present invention is illustrated by way of example and not by way of limitation in the figures of the accompanying drawings, in which the like references indicate similar elements and in which.

DETAILED DESCRIPTION OF THE INVENTION

Described is a method and apparatus for bead separation. In one embodiment, the method and apparatus causes beads within a fluid container (e.g., the wells of a micro-plate) to uniformly distribute about the base of the container to produce a "flat" profile. In addition, the method an apparatus causes the "flat" profile to form in an expedient manner, significantly increasing the throughput for bead separation.

In the following description, various aspects of the present invention will be described. However, it will be apparent to those skilled in the art that the present invention may be practiced with only some or all aspects of the present invention. For purposes of explanation, specific numbers, materials and configurations are set forth in order to provide a thorough understanding of the present invention. However, it will also be apparent to one skilled in the art that the present invention may be practiced without the specific details. In other instances, well-known features are omitted or simplified in order not to obscure the present invention.

Various operations will be described as multiple discrete steps in turn, in a manner that is most helpful in understanding the present invention. However, the order of description should not be construed as to imply that these operations are necessarily order dependent. In particular, these operations need not be performed in the order of presentation. Lastly, repeated usage of the phrase "in one embodiment" does not necessarily refer to the same embodiment, although it may.

Figure 1:
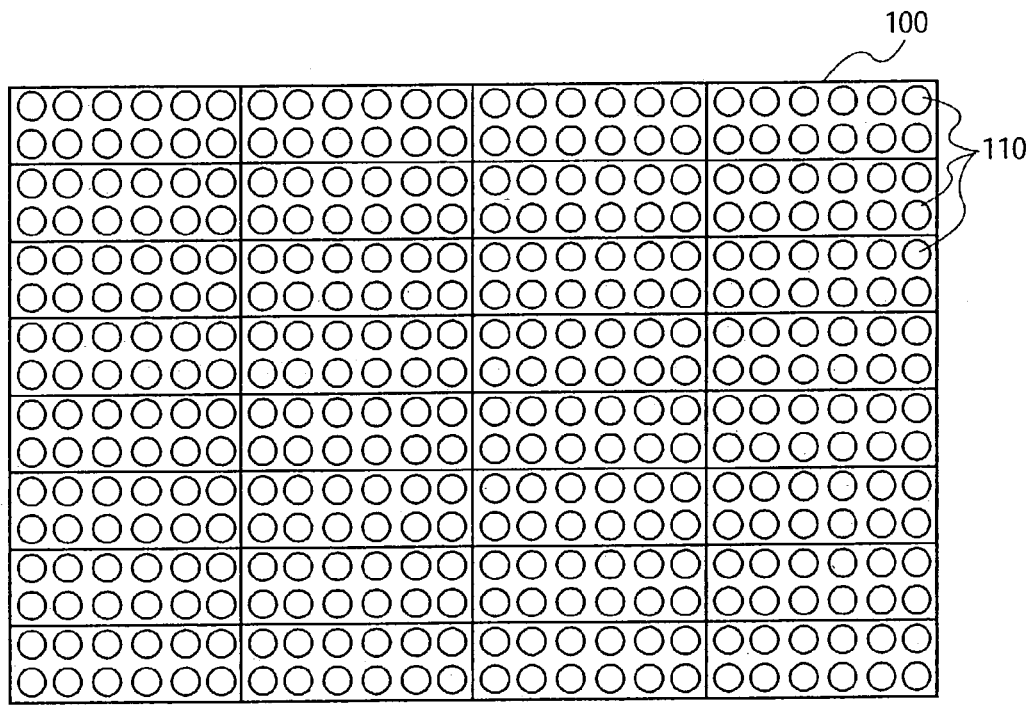
FIG. 1 illustrates a micro-plate upon which the invention may be practiced.

FIG. 1 illustrates a micro-plate upon which the invention may be practiced. FIG. 1 is a plan view of a 384-well micro-plate 100 having wells 110 arranged in a 16×24 configuration. Each of the wells 110 is capable of holding a hydrous solution. Although the wells illustrated are substantially circular, other geometric shapes are contemplated, for example, substantially square or even oval wells may be utilized. In the embodiment of FIG. 1, the profile view of the bottom portion of each well is rectangular. However, wells with other bottom profiles such as a concave shaped profile, or even a convex shaped profile may be used. Although FIG. 1 illustrates a 384-well micro-plate, it should be appreciated by one skilled in the art that the invention may be practiced upon a wide range of containers used for magnetic separation of materials such as, but not limited to, 96-well micro-plates, 1536-well micro-plates, tubes, Petri dishes, pipettes, beakers, and bottles each container comprising various shapes and dimensions.

Figure 2:
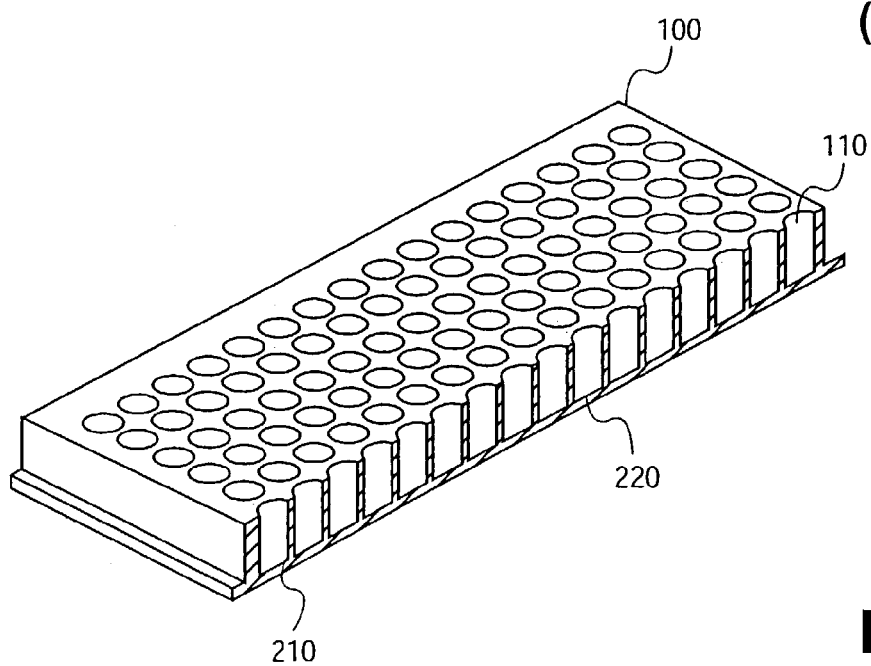
FIG. 2 illustrates a perspective view of a 384-well micro-plate.

FIG. 2 illustrates a perspective view of a 384-well micro-plate 100. As shown in FIG. 2, because of tightly packed density of wells, little or no space is available between the wells for the placement of magnets. Thus, depending on the tray configuration, there may be nowhere else to place a magnet other than below the tray.

Figure 3:
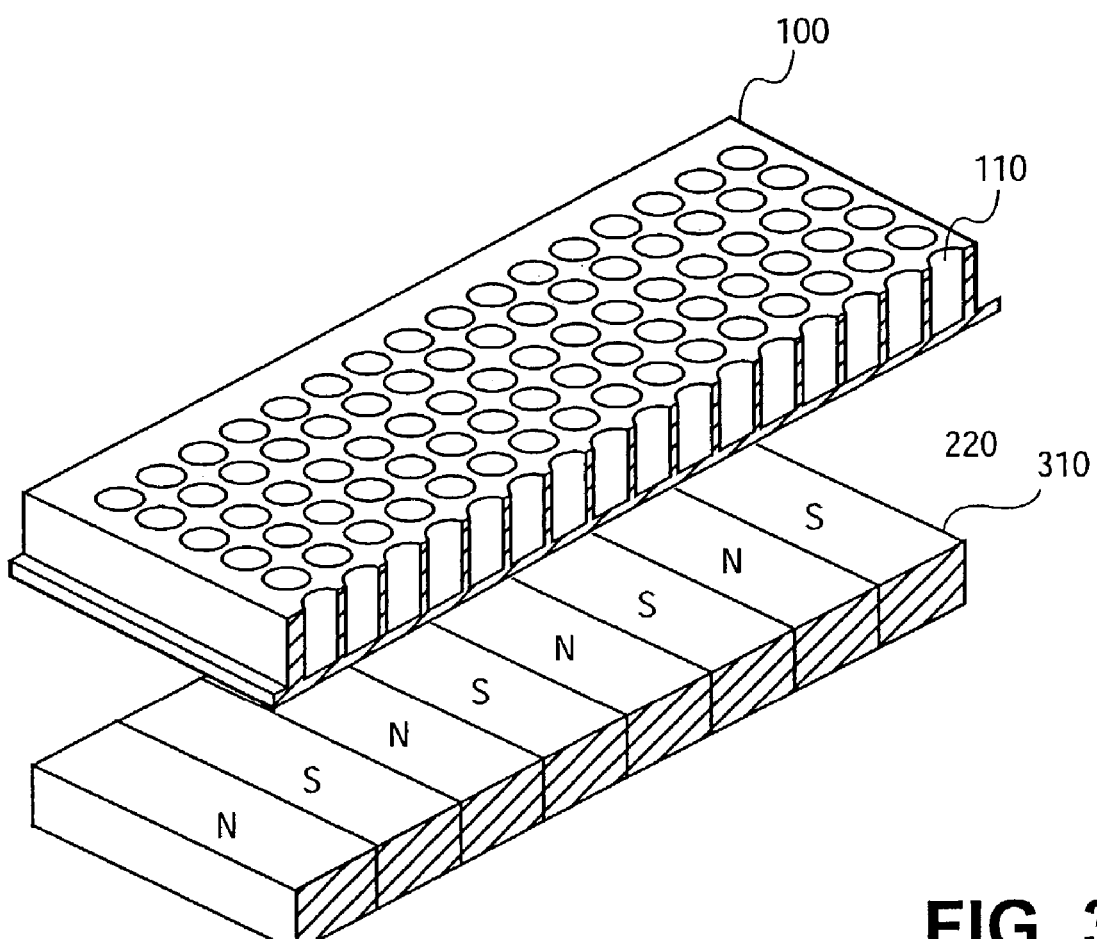
FIG. 3 illustrates a perspective view of a prior art embodiment of a magnetic arrangement used in bead separation.

FIG. 3 illustrates a perspective view of a prior art embodiment of a magnetic arrangement used in bead separation. As illustrated in FIG. 3 magnetic arrangement 310 facilitates the separation of particles in the wells by placement of the magnetic arrangement below the wells. As FIG. 3 illustrates, the magnetic arrangement 310 comprises a set of rectangular shaped permanent bar magnets placed below the wells in micro-plate 100. Each bar magnet in the magnetic arrangement 310 generates a north-south magnetic field parallel to the plane of the wells 110 containing the beads, and produces a magnetic gradient that is directed downwards and to the side of each well. One disadvantage of this magnet configuration is that the separation of beads is not uniform across the wells—that is, while there may be separation of the beads to the same location in each well, the relative force density, as defined above, is not uniform across every well. This leads to separation profiles that vary from one well to the next, depending on bead characteristics.

Figure 4:
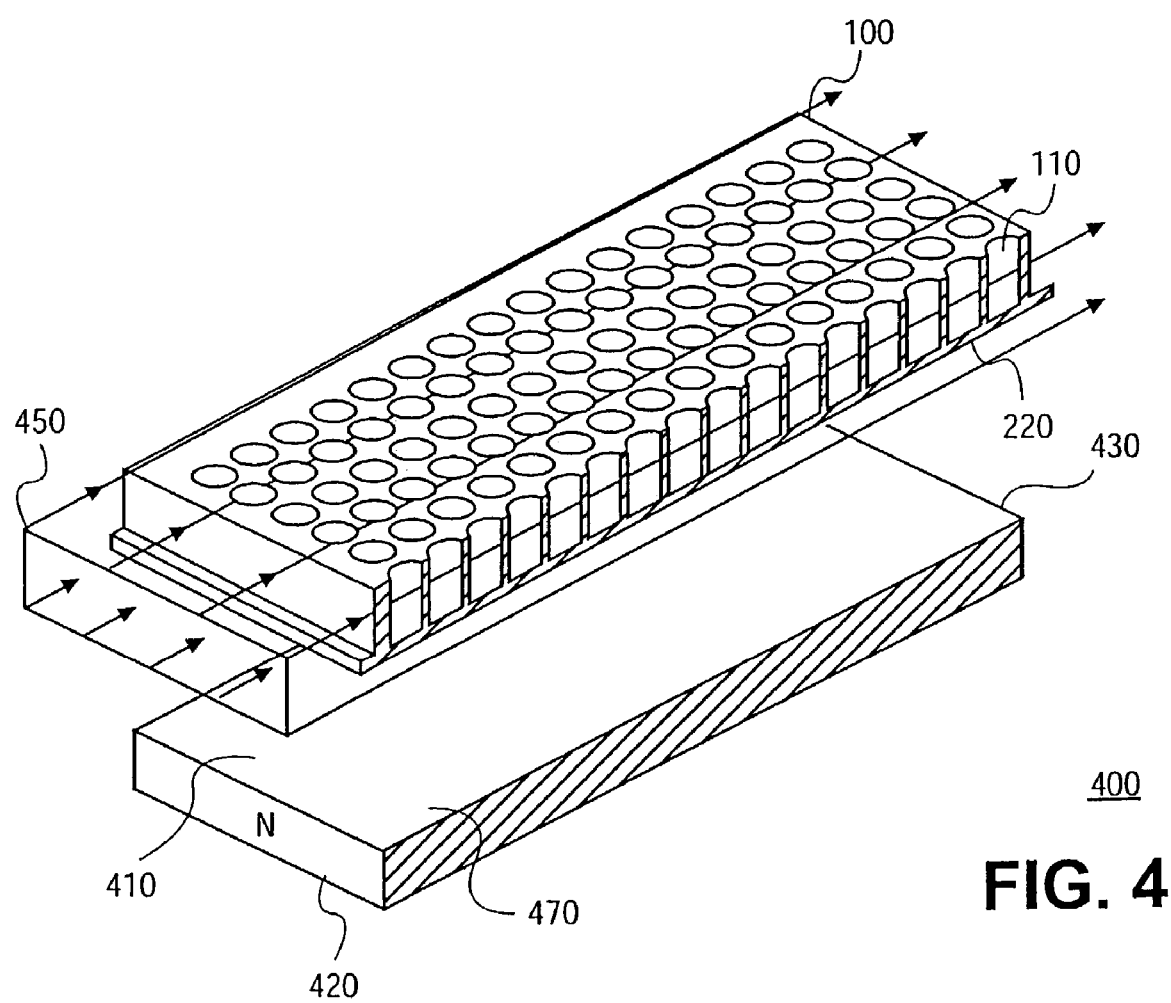
FIG. 4 illustrates a perspective view of one embodiment of a bead separation apparatus.

FIG. 4 illustrates a perspective view of one embodiment of a bead separation apparatus, in accordance with the invention. The bead separation apparatus 400 illustrated in FIG. 4 comprises a magnet 410 positioned beneath micro-plate 100 to accumulate beads in an expedient manner at the bottom of the wells with a uniform profile. In particular, a rectangular shaped magnet 410 (made of e.g., neodymium-iron-boron, samarium cobalt, etc.) is positioned below the base 220 of micro-plate 100 (i.e., the magnet is positioned such that the volume occupied by the micro-plate is within the influence of the magnetic field generated by the magnet). The rectangular shaped magnet has a first pole-face 420 (e.g., a north pole face) that is perpendicular to the transverse cross-sectional plane 470 of magnet 410. Similarly, the rectangular shaped magnet has a second pole-face 430 (i.e., a south pole face) that is opposite the first pole-face 420, and is also perpendicular to the transverse cross-sectional plane 470 of magnet 410. The pole-faces of the magnets illustrated in FIG. 4 are perpendicular to the transverse cross-sectional plane 470 of magnet 410 (i.e., the angle between the pole face and the transverse cross-section of the magnet 410 is ninety degrees). However, magnets having pole faces that are not perpendicular to the cross-sectional plane 470 but form an angle that may be either greater than ninety degrees or even less than ninety degrees with the cross-sectional plane 470 may also be used.

Magnet 410 generates a magnetic field 450 that is substantially parallel to the top plane 470 of the magnet. The magnetic field 450 generated by magnet 410 extends upward with a substantially parallel orientation from the plane of magnet 410 into the volume encompassed by micro-plate 100. The magnetic field 450 generated by magnet 410 maintains its substantially parallel orientation when penetrating the fluid containing the beads and has a substantially uniform strength along the entire surface of micro-plate 100. However, the magnetic field may exhibit some orthogonal components at the extremities of the magnet. This is acceptable, however, as the downward gradient at these locations is greater than at the center of the magnet. Additionally, the parallel component of the flux density may vary slightly throughout the volume, without departing from the invention.

As illustrated in the embodiment of FIG. 4 the substantially parallel magnetic field with a downward oriented gradient causes the beads within the wells in the micro-plate to expediently accumulate at the bottom of the wells with a flat, or horizontal, separation profile. The dot product of the parallel component of the flux density at all locations in the volume and the gradient produces a substantially uniform relative force density about the entire volume.

Although the embodiment of FIG. 4 illustrates magnet 410 disposed below base 220 of micro-plate 100, in alternative embodiments magnet 410 may be disposed proximate to and above the wells of micro-plate 100 to collect the beads at the top of the wells (i.e., the volume occupied by the micro-plate is within the influence of the magnetic field generated by the magnet). In still other embodiments, magnet 410 may be disposed proximate the sides of the wells of micro-plate 100 to collect beads at the sidewalls of the wells in micro-plate 100.

Although, the embodiment of FIG. 4 illustrates a rectangular shaped magnet 410, one or more magnets of other shapes (e.g., square, triangular, hexagonal, trapezoidal, circular, elliptical, cylindrical etc.) may alternatively be used so long as the magnets generate a uniform parallel magnetic field, that extends into part or all of the volume occupied by micro-plate 100 and has a uniform gradient directed toward the surface of the magnet.

Figure 5:
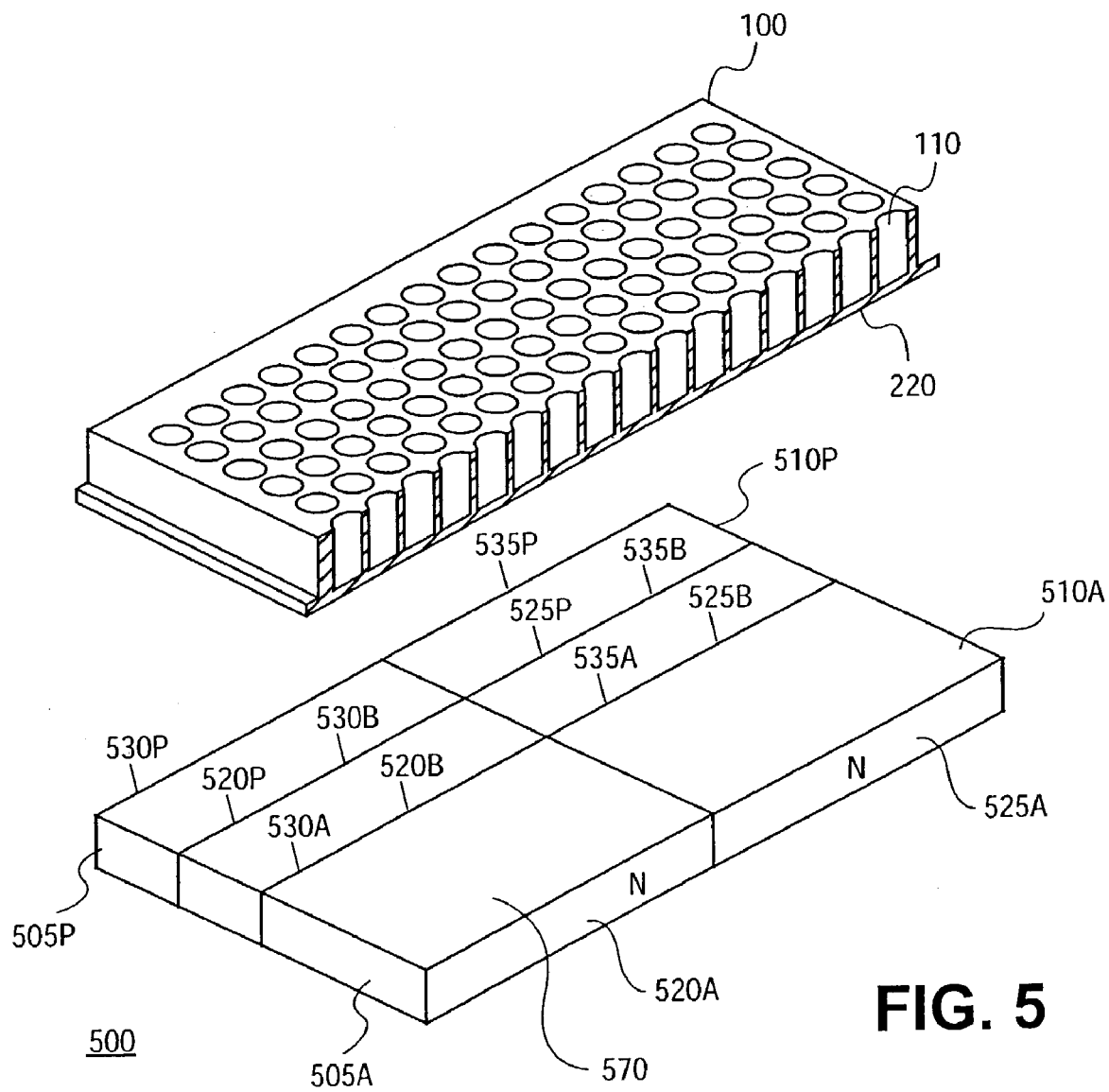
FIG. 5 illustrates a perspective view of one embodiment of a magnetic arrangement used for bead separation.

FIG. 5 illustrates a perspective view of one embodiment of a magnetic arrangement used for bead separation. FIG. 5 illustrates a magnet arrangement 500 having a set of one or more rectangular shaped magnets that are positioned below the base 220 of micro-plate 100 (i.e., the magnets are positioned such that the volume occupied by the micro-plate is within the influence of the magnetic field generated by the magnet arrangement). Each magnet in the set of magnets may be encased in a protective cladding. Each set of magnets in magnet arrangement 500 is made up of one or more rows of rectangular shaped magnets 505A–505P and 510A–510P. Each magnet in the set of rows 505A–505P, and 510A–510P has a first pole-face (e.g., a north-pole face) 520A–520P and 525A–525P that is perpendicular to the transverse cross-sectional plane 570 of magnet arrangement 500. Similarly, each magnet in the set of rows 505A–505P, and 510A–510P has a second pole-face (i.e., a south pole face) 530A–530P and 535A–535P that is opposite the corresponding first pole-face 520A–520P and 525A–525P respectively. The second pole-face is also perpendicular to the transverse cross-sectional plane 570 of magnet arrangement 500. Thus for the row of magnets 505A–505P, the south pole-face 530A of magnet 505A is in contact with the north pole-face 520B of magnet 505B, and the south pole-face 530B of magnet 505B is in contact with the north pole-face 520P of magnet 505P. So also for adjacent row 510A–510P, the north pole-face 525B of magnet 510B is in contact with the south pole-face 535A of magnet 510A, and the south pole-face 535B of magnet 510B is in contact with the north pole-face 525P of magnet 510P. The magnets in each row 505A–505P and 510A–510P are adjacent to each other and are in contact with each other such that the pole-faces of the magnets in each row are coplanar.

The magnet arrangement 500 of FIG. 5 generates a substantially uniform magnetic field that extends into all or part of the volume occupied by micro-plate 100. The magnetic field generated by the magnet arrangement 500 is substantially parallel to the transverse cross-sectional surface of the wells in the micro-plate, and has a substantially uniform gradient directed toward the surface of the magnet arrangement.

The substantially uniform parallel magnetic field in combination with the substantially uniform gradient directed toward the surface of the magnet arrangement causes beads within the wells to achieve a uniform profile. For example, the magnet configuration causes the beads to accumulate expediently at the bottom of the wells in a flat, or horizontal, profile.

Figure 6:
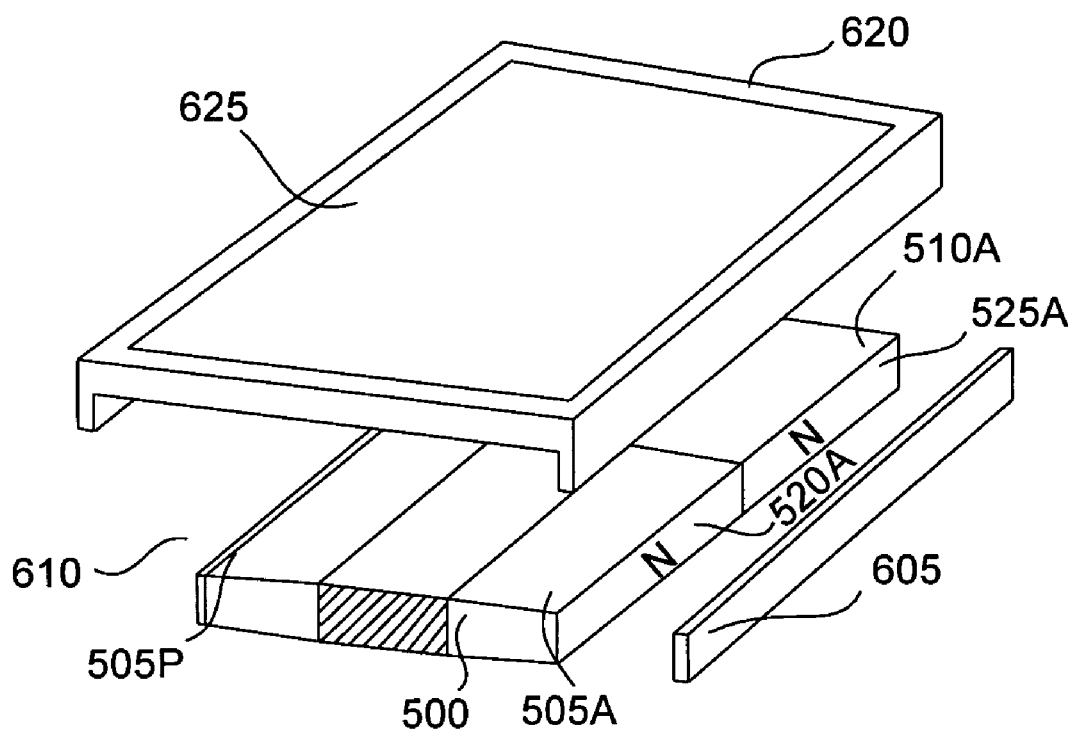
FIG. 6 illustrates a perspective view of one embodiment of a housing for a magnet arrangement.

FIG. 6 illustrates a perspective view of one embodiment of a housing for a magnet arrangement. As FIG. 6 illustrates, magnet arrangement 500 includes one or more rows of magnets that have like pole-faces adjacent to each other. In order to keep the like pole-faces of the magnets in magnet arrangement 500 from repelling each other, the magnets are glued together and placed in a housing 620. Housing 620 has an opening in base 625 that is machined to receive and to align base 220 of micro-plate 100 such that the magnet arrangement 500 generates a uniform parallel magnetic field that extends into part or all of the volume occupied by micro-plate 100. The uniform parallel magnetic field generated by magnet arrangement 500 has a uniform gradient that is directed toward the surface of the magnet arrangement.

Housing 620 is made of non-magnetic materials (e.g., aluminum, berillium copper, glass, plastic etc.) so that the housing material does not distort the magnetic field generated by magnet arrangement 500.

In one embodiment, one or more of the magnets at the ends of rows 505A–505P and 510A–510P may be tapered toward the outer edge (see, e.g., magnets 505A, 505P, 510A and 510P of FIG. 6) to produce a magnetic field as described above.

In one embodiment, a first pole-piece 605 made of ferromagnetic material may be placed in contact with pole-faces 520A and 525A, and a second pole-piece 610, also made of ferro-magnetic materials, may be placed in contact with pole-faces 530P and 535P to contribute to the uniform parallel nature of the magnetic field generated by magnet arrangement 500.

Figure 7:
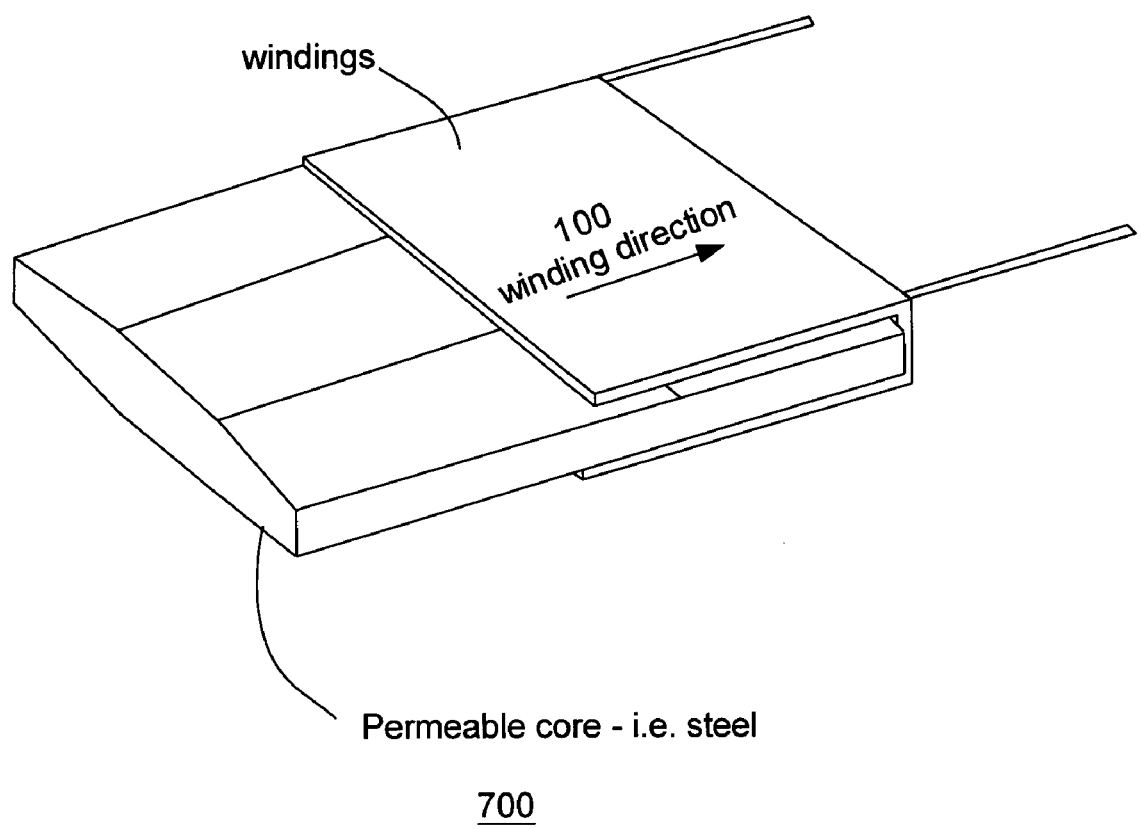
FIG. 7 illustrates one embodiment of a single axis Helmholtz coil used in bead separation.

FIG. 7 illustrates one embodiment of an electromagnet used in bead separation. When a source of DC power 720 is applied to the circuit a substantially parallel uniform magnetic field is produced about a certain volume within the area of the electromagnet. By placing the micro-plate 100 within the magnetic field, such that the transverse cross-sectional plane of the wells is substantially parallel to the magnetic field generated by the electromagnet, the beads contained in the wells of the micro-plate accumulate expediently at the bottom of the wells with a uniform profile.

In one embodiment, multiple electromagnets may be used wherein each electromagnet is independently controlled using a dedicated power supply. By independently controlling the current through the electromagnets the magnetic field including the magnetic gradient of the field generated by each electromagnet can be regulated to complement other electromagnets in providing the desired substantially parallel uniform magnetic field having a substantially uniform downward gradient over a specified sample volume.

In general, those skilled in the art will recognize that the invention is not limited by the details described, instead, the invention can be practiced with modifications and alterations within the spirit and scope of the appended claims. The description is thus to be regarded as illustrative instead of restrictive on the invention.

What is claimed is:

1. A magnetic separation apparatus comprising:
   a container:
   a magnet with a pole oriented in a direction nonperpendicular to a transverse cross-sectional plane of the container, the magnet positioned at least one of under or over a portion of the container to generate a substantially uniform north-south magnetic field, the substantially uniform north-south magnetic field oriented substantially parallel with the transverse cross-sectional plane of the container, the substantially uniform north-south magnetic field extending into a part or all of a volume occupied by the container, the substantially uniform north-south magnetic field having a substantially uniform magnetic gradient directed toward a transverse cross-sectional plane of the magnet to separate magnetically susceptible particles in a fluid contained in the container.

2. The apparatus as in claim 1 further comprising a first pole-piece coupled to a first magnetic pole-face and a second pole-piece coupled to a second magnetic pole-face.

3. The apparatus as in claim 2 wherein the magnet is tapered toward at least one of the first pole-piece and the second pole-piece.

4. The apparatus as in claim 1 wherein the container comprises a multi-well micro-plate.

5. The apparatus as in claim 4 wherein the multi well micro-plate is selected from the group consisting of a 96-well micro-plate, a 384-well micro-plate, and a 1536-well micro-plate.

6. The apparatus of claim 1, wherein the container is selected from the group consisting of a tube, a vial, a Petri dish, and a bottle.

7. The apparatus as in claim 1, wherein the magnet is enclosed within a protective housing.

8. The apparatus as in claim 1, wherein the magnet is selected from the group consisting of a polygonal shaped magnet, a cylindrical shaped magnet, a circular shaped magnet, and an elliptical shaped magnet.

9. A magnetic separation apparatus comprising:
an electromagnet to generate a substantially uniform parallel magnetic field;
a container comprising a plurality of particles and a plurality of magnetically susceptible particles placed in the substantially uniform parallel magnetic field such that the substantially uniform parallel magnetic field is substantially parallel with a transverse cross-section of the container, has a gradient across a plane substantially perpendicular to the transverse-cross-sectional plane of the container, and extends into the container, to separate the plurality of magnetically susceptible particles from the plurality of particles in the container.

10. The apparatus as in claim 9, wherein the container comprises a multi-well micro-plate.

11. The apparatus as in claim 10 wherein the multi well micro-plate is selected from the group consisting of a 96-well micro-plate, a 384-well micro-plate, and a 1536-well micro-plate.

12. The apparatus of claim 9, wherein the container is selected from the group consisting of a tube, a vial, a Petri dish, and a bottle.

13. The Apparatus of claim 9 further comprising:
at least a second electromagnet, wherein each electromagnet is independently controlled using a dedicated power supply.

14. A method for magnetic separation comprising:
arranging one or more magnets in a plane, with one or more poles oriented in a direction nonperpendicular to a transverse cross-sectional plane of a container, the one or more magnets positioned at least one of under or over a portion of the container to generate a uniform north-south magnetic field oriented parallel with the transverse cross sectional plane of the container, the uniform north-south magnetic field extending into a volume occupied by the container, the uniform north-south magnetic field having a uniform magnetic gradient directed toward a transverse cross-sectional plane of the one or more magnets;
receiving in the container a plurality of particles along with a plurality of magnetically susceptible particles; and
separating the magnetically susceptible particles from the plurality of particles when the one or more magnets apply the north-south magnetic field.

15. The method as in claim 14, wherein the container comprises a multi-well micro-plate.

16. The method as in claim 14, wherein the container is selected from the group consisting of a tube, a vial, a Petri dish, and a bottle.

17. The method as in claim 14, wherein magnet is selected from the group consisting of polygonal shaped magnet, a circular shaped magnet, and an elliptical shaped magnet.

18. A magnetic separation apparatus comprising:
a first magnet having a first pole-face non-parallel to a transverse cross-sectional plane of the first magnet to generate a substantially uniform north-south magnetic field;
a container positioned over or under the first magnet, the container having a vertical axis perpendicular to the transverse cross-sectional plane of the first magnet, the vertical axis intersecting an open end of the container and the first magnet, wherein the substantially uniform north-south magnetic field extends into a volume within the container and is oriented substantially parallel with a transverse cross-sectional plane of the container volume.

19. The magnetic separation apparatus of claim 18, further comprising:
a second magnet having a first pole-face non-parallel to a transverse cross-sectional plane of the second magnet, the first pole-face of the second magnet adjacent to the first pole-face of the first magnet to form a magnet arrangement having a transverse cross-sectional plane parallel to the transverse cross-sectional planes of the first and second magnets.

20. The magnetic separation apparatus of claim 19, wherein the first pole-face of the first magnet is the same polarity as the first pole-face of the second magnet.

21. The magnetic separation apparatus of claim 18, wherein the first pole-face is perpendicular to the transverse cross-sectional plane.

22. The magnetic separation apparatus of claim 18, wherein the first magnet is tapered toward the first pole-face.

23. The apparatus as in claim 18 wherein the container is a well in a multi-well micro-plate, the microplate having a base substantially parallel to the transverse cross-sectional plane of the first magnet.

* * * * *